United States Patent
Treado et al.

(10) Patent No.: US 7,420,664 B2
(45) Date of Patent: Sep. 2, 2008

(54) SYSTEM AND METHOD FOR ROBOT MOUNTED SENSOR

(75) Inventors: Patrick J. Treado, Pittsburgh, PA (US); Charles W. Gardner, Jr., Gibsonia, PA (US)

(73) Assignee: ChemImage Corporation, Pittsburgh, PA (US)

( * ) Notice: Subject to any disclaimer, the term of this patent is extended or adjusted under 35 U.S.C. 154(b) by 55 days.

(21) Appl. No.: 11/484,939

(22) Filed: Jul. 12, 2006

(65) Prior Publication Data

US 2008/0165344 A1    Jul. 10, 2008

Related U.S. Application Data

(60) Provisional application No. 60/699,284, filed on Jul. 14, 2005.

(51) Int. Cl.
*G01N 21/00* (2006.01)
(52) U.S. Cl. .......................................... 356/72; 901/47
(58) Field of Classification Search ............. 356/72–73, 356/318, 301; 901/10, 46–47
See application file for complete search history.

(56) References Cited

U.S. PATENT DOCUMENTS

| | | | | |
|---|---|---|---|---|
| 4,618,758 | A  * | 10/1986 | Gilli et al. ............... | 219/121.67 |
| 4,956,923 | A  * | 9/1990 | Pettingell et al. .............. | 33/558 |
| 6,657,721 | B1 * | 12/2003 | Palleschi et al. ............ | 356/318 |
| 6,717,668 | B2 * | 4/2004 | Treado et al. ................ | 356/327 |
| 2006/0158647 | A1 * | 7/2006 | Yao ............................ | 356/326 |

* cited by examiner

*Primary Examiner*—Kara E Geisel
(74) *Attorney, Agent, or Firm*—Morgan, Lewis & Bockius LLP

(57) ABSTRACT

An apparatus and method for the remote analysis and identification of unknown compounds. A robotic arm positions a sensor on a surface. The sensor unit has a monitoring mechanism to monitor separation between the sensor unit and the surface when placed in contact with the surface to maintain the separation substantially constant. An illumination source illuminates the region of interest to produce scattered photons from an unknown compound. The scattered photons are collected by an optical system and delivered to a spectroscopic detector for analysis and identification. An algorithm is applied to the data generated by the spectroscopic detector to identify the unknown compound.

16 Claims, 10 Drawing Sheets

SYSTEM AND METHOD FOR ROBOT MOUNTED SENSOR

RELATED APPLICATIONS

This application claims the benefit of U.S. Patent Application No. 60/699,284, filed Jul. 14, 2005, entitled Raman Bio Identification (RBI) the Robot, which is incorporated herein by reference in its entirety.

FIELD OF DISCLOSURE

This application relates generally to apparatus and methods for the remote analysis and identification of chemical, biological, explosive or nuclear agents.

BACKGROUND

Many detection systems exist for the detection of a variety of chemical, biological, explosive and nuclear agents. While these devices work very well at detecting their targeted agents, they have a number of drawbacks. Firstly, the devices generally only detect one or a few types of certain agents at the same time. A range of assays is used to optimize detection for the expected threats, but broad-spectrum simultaneous detection is generally not possible. Secondly, these devices must be brought into contact with the sample being analyzed—i.e. proximity to the threat is required. This means that soldiers or first responders are exposed to potential contaminants in order to acquire samples. Because of how they are typically used, these devices are designed as handheld or worn by soldiers. This makes interfacing with the devices via computer or other electronic means cumbersome.

Solutions that at least partially address these shortcomings have been developed. In particular, a CHARS ["Chemical weapons Hazardous Gas And Radiation System"] system is designed to mount on a small unmanned ground vehicle (UGV). The system includes three standard sensors: the MultiRAE™ hazmat environmental gas sensor, the Joint Chemical Agent Detect (JCAD) nerve, blister and blood agent sensor, and the Can berra AN/URD Radiac 13 gamma and neutron radiation detector. CHARS directly addresses all three of the issues mentioned above to a certain degree—by using multiple sensors packaged together, a broader spectrum of threat agents can be detected; the use of UGV significantly reduces the risks to the human through a special hardware configuration; and users upload data remotely from all sensors using a common communication protocol. While a significant advance, the CHARS package does also suffer from several drawbacks, of which the two most significant are: (i) no support for the detection of bio-warfare agents, and (ii) the need to package (and support) multiple individual sensors to get broad-spectrum threat coverage.

The present disclosure describes a reagent free mobile sensor to detect and identify a sample that may contain chemical, biological, explosive, or nuclear agent(s). The present disclosure describes an approach that maintains a substantially constant distance between the sensor and the surface undergoing analysis.

SUMMARY

The present disclosure provides for an apparatus and method for the remote analysis and identification of unknown compounds. The apparatus includes a robotic arm and a sensor unit that are operatively coupled. The sensor unit has a monitoring mechanism configured to physically contact a surface in a region of interest. The monitoring mechanism is configured to monitor separation between the sensor unit and the surface when placed in contact with the surface to maintain the separation substantially constant.

In one embodiment, the monitoring mechanism includes a force sensor placed in contact with the surface and which generates an output signal. A feedback mechanism is coupled to the force sensor to receive the output signal and to maintain the output signal substantially constant by adjusting the separation between the force sensor and the surface in the region of interest.

The unknown compounds include bacterium, virus, protozoan, biological toxin, fungus, chemical agents, radiological material and explosive material.

In yet another embodiment, an illumination source illuminates the region of interest to produce scattered photons from the unknown compound. The scattered photons are collected by an optical system and delivered to a spectroscopic detector for analysis and identification.

In still another embodiment, a fiber array spectral translator device outputs collected photons to a spectrometer which analyzes the scattered photons using Raman spectroscopy to produce a plurality of spatially resolved Raman spectra. An algorithm is applied to the plurality of spatially resolved Raman spectra to identify the unknown compounds in the region of interest.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

In the drawings.

DESCRIPTION OF THE EMBODIMENTS

Reference will now be made in detail to the embodiments of the present disclosure, examples of which are illustrated in the accompanying drawings. Wherever possible, the same reference numbers will be used throughout the drawings to refer to the same or like parts.

The apparatus and method of the present disclosure provide for the reagentless analysis of water, soil and surfaces potentially exposed to chemical, biological, explosive or nuclear agents by transporting a detector directly to the sample. This approach permits elimination of almost all sources of sample contamination from the detection system.

In addition, human operators are not exposed to potential hazardous agents. This direct analysis system allows for the detector to take multiple measurements during a mission, thus reducing the time to characterize an incident scene.

Additionally the apparatus and method of the present disclosure provide for an apparatus that measures surface contaminants in a proximity mode where the sample is located less than 20 millimeters from the sensor and in a standoff mode where the sample is located at a distance of greater than one meter. In one embodiment, the apparatus of the present disclosure functions as a standoff Raman detector. In another embodiment, the apparatus of the present disclosure functions as a proximity Raman detector. In yet another embodiment, the apparatus of the present disclosure functions as a proximity Laser Induced Breakdown Spectroscopy ("LIBS") detector. In still another embodiment, the apparatus of the present disclosure functions as a standoff LIBS detector. In another embodiment the apparatus of the present disclosure functions as a combined Raman and LIBS standoff or proximity detector.

In one embodiment, an unknown compound is identified using Raman spectroscopy which presents the advantage in its lack of reagents. This minimizes the logistics chain necessary to operate the apparatus and eliminates the need to end a sampling mission due to a lack of reagent or perhaps, the wrong reagents. The lack of reagents and the broad applicability of Raman spectroscopy create the ability to detect and identify hundreds of chemical or biological agents in a single measurement, without any assumptions about the potential threat.

Figure 1:
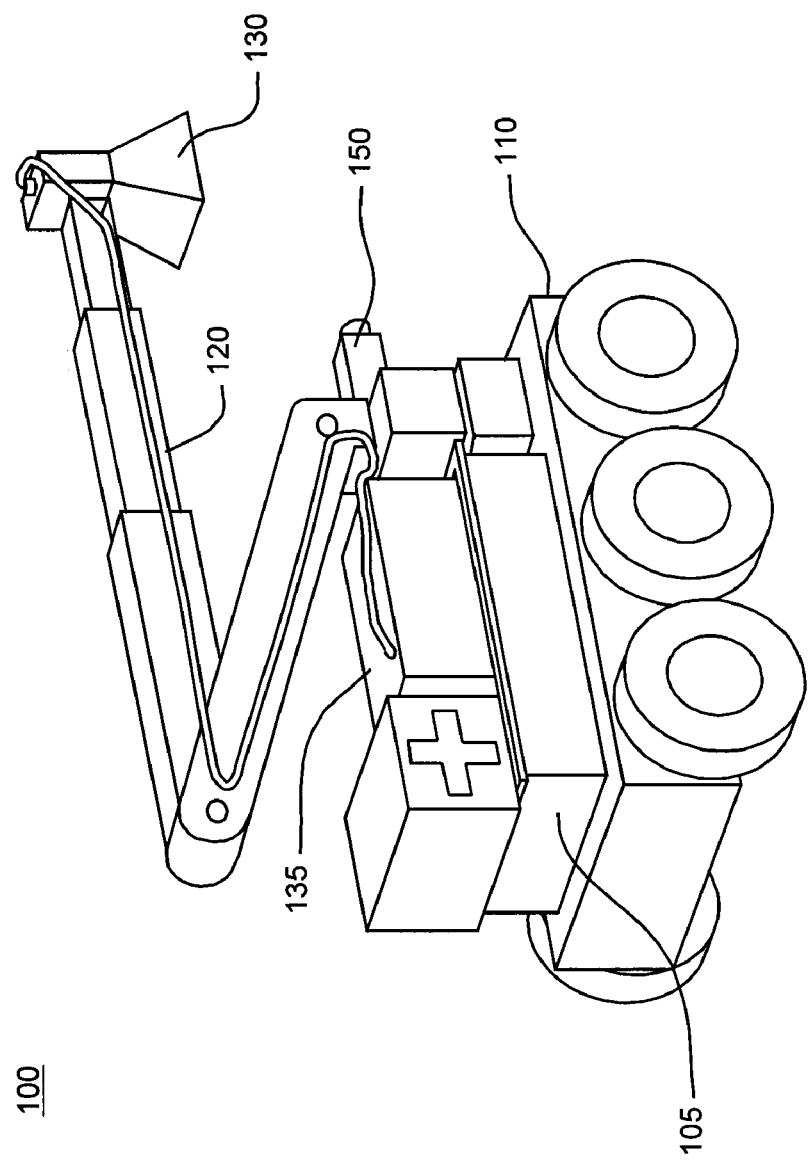
FIG. 1 illustrates an exemplary apparatus of the present disclosure.
Figure 3:
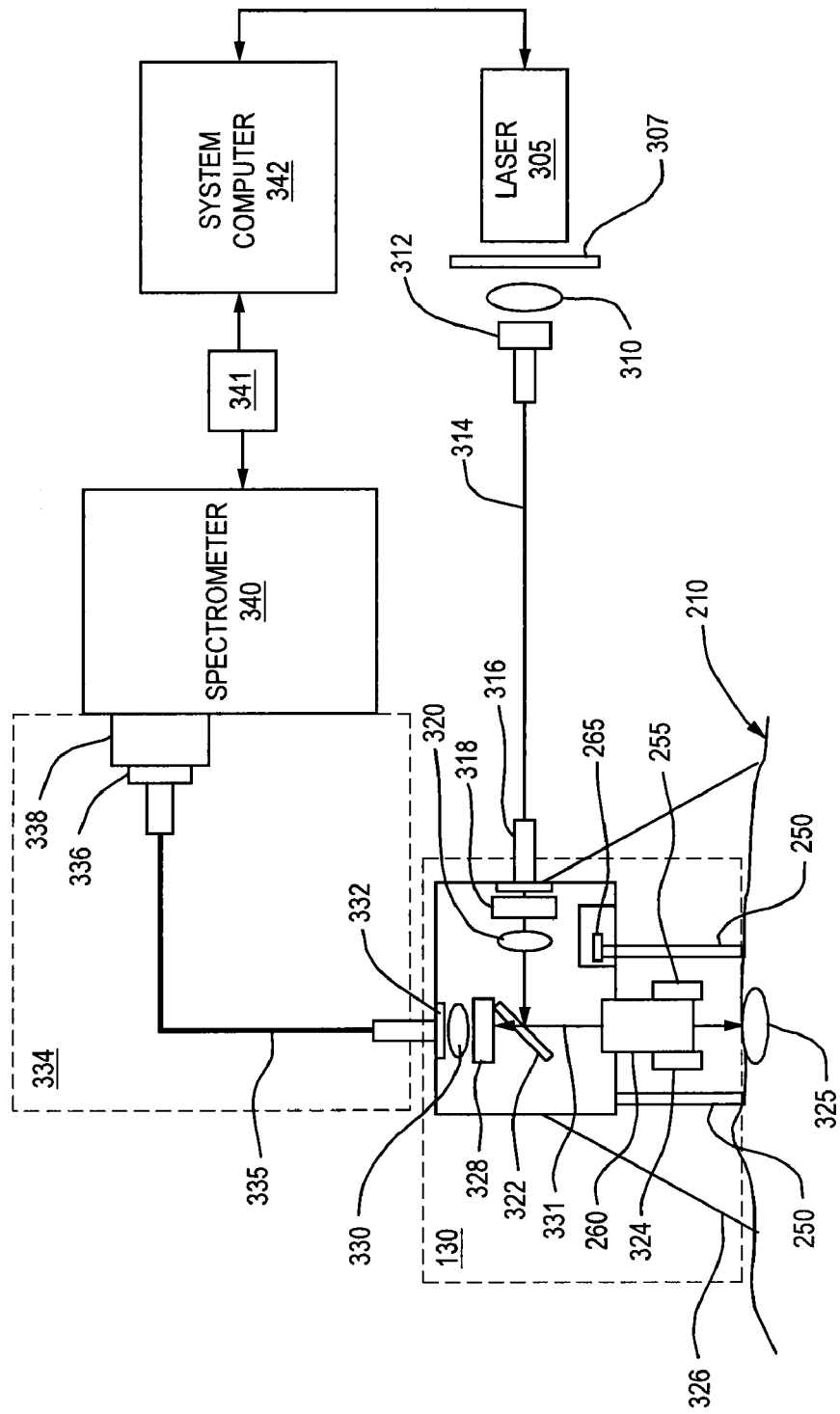
FIG. 3 illustrates another exemplary apparatus of the present disclosure.

FIG. 1 illustrates an exemplary apparatus 100 which may be used to carry out the methods of the present disclosure. Apparatus 100 includes an unmanned vehicle 110, a robot chassis 105, a robotic arm 120 and a sensor unit 130. Apparatus 100 allows for the separation of the sensor unit 130 from the instrument package 135 through the use of fiber optic coupling as illustrated in FIG. 3. The sensor unit 130 is operatively coupled to the robotic arm 120. This allows for the placement of sensor unit 130 on the robotic arm 120 with the instrument package 135 comprising the spectrometer and support electronics mounted on the robot base. The apparatus is deployed at a region of interest of suspected contamination to detect the presence of an unknown sample using spectroscopic measurements.

The unknown compound includes a single sample or a mixture of samples. The unknown includes a hazardous substance and a bacterium, virus, protozoan, biological toxin, fungus, a chemical agent, a radiological material and an explosive material. The bacterium includes *Anthrax, Bacillus, Streptococcus, Staphylococcus, Escherichia, Erwinia,* and *Pseudomonas*. The virus includes a pathogenic virus selected from smallpox, influenza and Ebola viruses. The biological toxin includes ricin. The hazardous substance is any substance that may cause disease, injury, discomfort, pain, or death to an animal such as a human. Examples of chemical explosives include dynamite, nitroglycerine, TNT, RDX, PETN, HMX, and an ammonium nitrate/fuel oil mixture.

In one embodiment, apparatus 100 includes an image capture device 150 to position the sensor unit 130 in the region of interest. The image capture device includes at least one of the following imaging devices: a visible light video capture device such as a CCD or CMOS video camera; a fluorescence imaging device using a CCD camera, typically cooled for lower background noise; an NIR (Near Infrared) imaging device employing an InGaAs or InSb focal plane array (FPA) camera; an MIR (Mid Infrared) imaging device employing a thermal or semiconductor FPA camera; a UV (Ultraviolet) imaging device using a UV-sensitized CCD camera; a hyperspectral imaging device using a tunable imaging spectrometer and suitable detector; and a tera Hertz (THz) imaging device using microbolometer or similar detection strategies.

In one embodiment, the sensor unit 130 includes a video capture device 150. In yet another embodiment, the video capture device includes a light source (not shown) to illuminate the surface. The light source includes an incandescent lamp or LED. For a UV LED light source operating at a wavelength range of 360 to 365 nm, auto fluorescence shown by most biothreat agents may be used to selectively target a region of interest that may have biothreat contamination and warrant interrogation with the sensor unit 130. In another embodiment, the optics system of the video capture device is selected to allow a large depth of focus over a wide range of working distance.

In yet another embodiment, the image capture device includes a LIBS (Laser Induced Breakdown Spectroscopy) device to target the region of interest for an unknown sample. LIBS may also be used to identify the unknown compound in the region of interest.

Figure 2A:
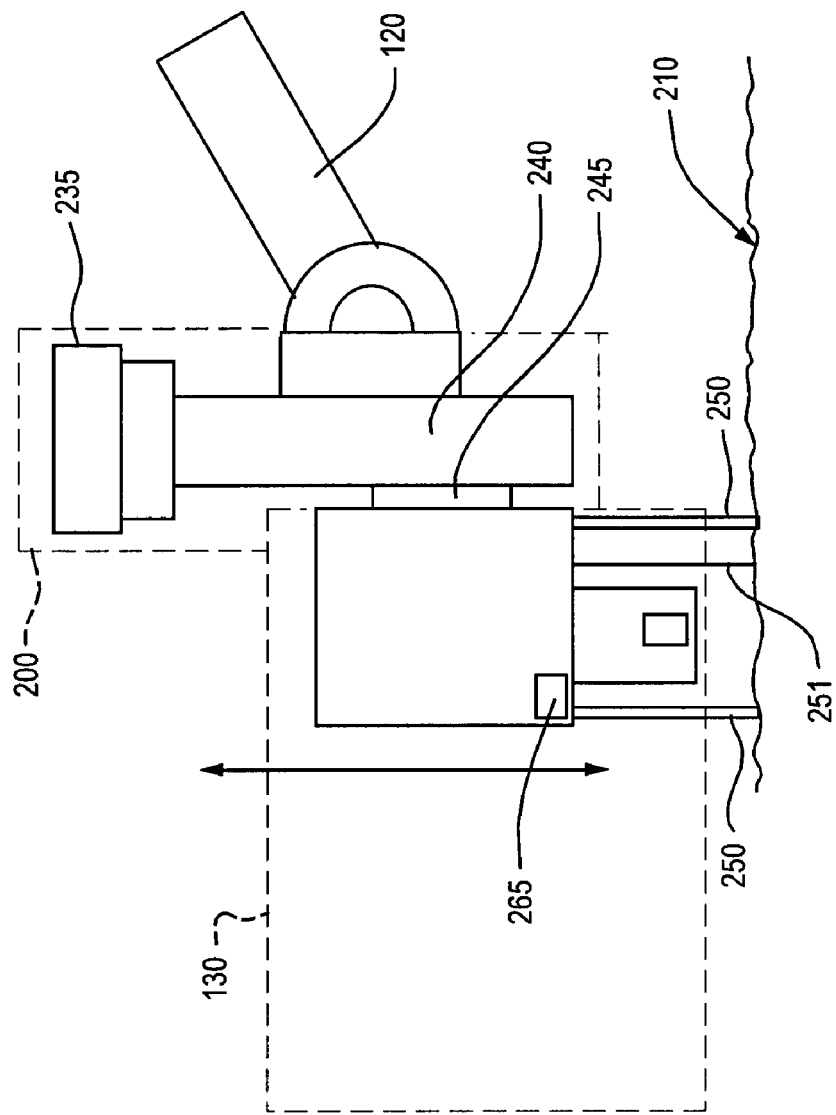
FIGS. 2A and 2B illustrate an embodiment of the present disclosure.

FIG. 2A illustrates an exemplary fine positioning device 200. The fine positioning device includes a stepper motor 235, a vertical linear stage 240, a stage slider 245, a plurality of rods 250, and force sensor 265. The stepper motor 235 operates the linear stage 240 to move the sensor unit 130 in vertical direction. The linear stage 240 may be positioned between the robotic arm 120 and the sensor unit 130. In one embodiment, the linear stage 240 is driven with a precision lead screw (not shown). A plurality of rods 250 limits the distance from the sensor unit 130 to the surface 210. The linear stage 240 moves the sensor unit 130 in the vertical direction until the rods 250 contact the surface 210 being analyzed. This approach ensures that the sensor unit 130 is operating at the correct WD ("Working Distance") 251. Working distance 251 is defined as the distance between the collection optic surface and the unknown. The properties of focal length and NA determine the optimum working distance 251 for the lens.

Figure 2B:
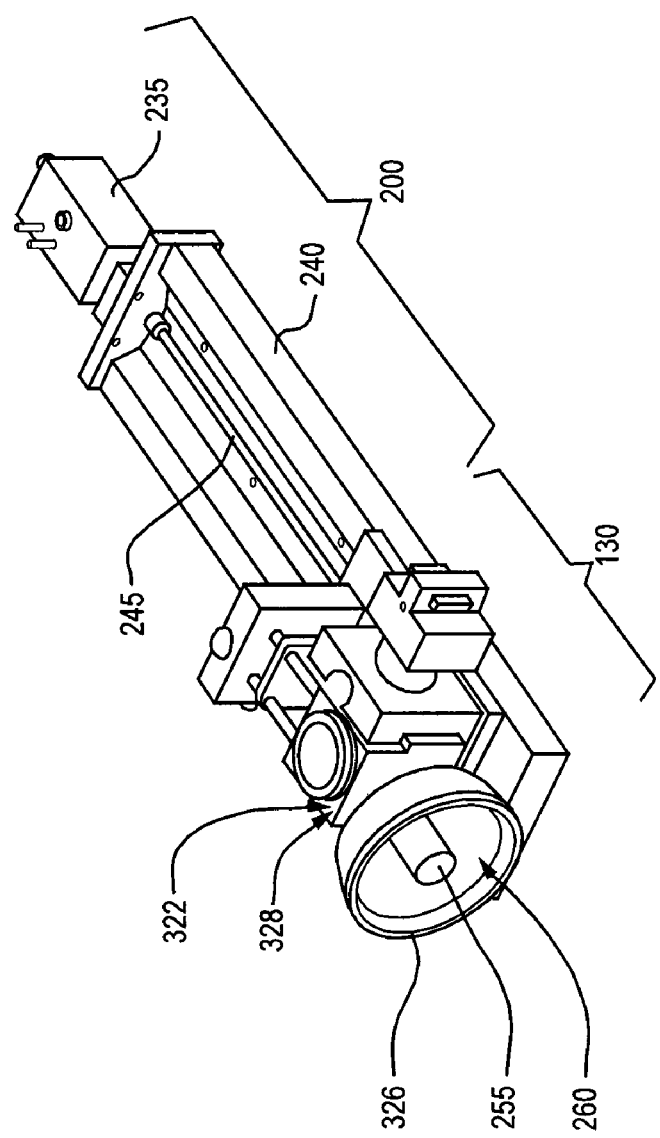

FIG. 2B illustrates another exemplary fine positioning device 200. This device 200 is based on a linear slide 240 (Velmex, Inc., Model MA4015B-S4) driven by a NEMA 17 stepper motor 235 with integral serial control (Zaber Technologies, Model T-NM17C200) (not shown). This stepper motor 235 has a resolution of 0.028 degrees per step. The lead screw 245 on the stage has a pitch of 0.050 inches per revolution. Therefore, the resolution of the fine positioning device 200 is on the order of 0.1 µm per step. FIG. 2B also illustrates the coupling of sensor unit 130 to the fine positioning device 200. The components of the sensor unit 130 illustrated in FIG. 2B include a dichroic beam splitter 322, a laser rejection filter 328, a light shield 326, a video camera 255 and objective lens 260.

The positioning of sensor unit 130 is controlled by the fine positioning device 200. The fine positioning device 200 is positioned between the sensor unit 130 and the robotic arm 120 to incrementally move the sensor unit 130 relative to the surface 210 in the region of interest (not shown). In one embodiment, the fine positioning device 200 has a tolerance of 40 micrometers or less from the sensor position above the unknown.

Referring again to FIG. 2A, the fine positioning system 200 includes a monitoring mechanism having a feedback control mechanism (not shown), to compensate for vertical movement of the robotic arm 120 during an analysis of the unknown. In one embodiment, the monitoring mechanism includes a force sensor 265 and a plurality of rods 250 that contact the surface 210 and generates an output signal. The monitoring mechanism is configured to physically contact surface 210 in the region of interest (not shown). To maintain a substantially constant separation 251 between the sensor unit 130 and the surface 210, the monitoring mechanism is configured to monitor the separation 251 when sensor unit 130 is placed in contact with the surface 210. A feedback mechanism (not shown) is coupled to the force sensor 265 to receive the output signal and to maintain the output signal substantially constant by adjusting the separation between the sensor unit 130 and the surface 210 thereby keeping a constant force between the sampling surface and the probe rod. For the purposes of this application, the term substantially constant means plus or minus five percent. In another embodiment, force sensor 265 is coupled to one of the rods 250.

FIG. 3 further illustrates an exemplary apparatus of the present disclosure. The apparatus includes a laser light source 305 to illuminate a surface 210 having an unknown 325. The illumination produces scattered or reflected photons from different locations on or within the unknown 325. In one embodiment, the laser light source 304 is a 532 nm diode-pumped solid-state (DPSS) laser operating in the range of 25 to 500 mW. The output from the laser light source 305 may be passed through a laser focus lens 310 to couple the laser light into a multimode silica fiber 314 using suitable fiber position devices 312 and 316. In another embodiment of FIG. 3, a laser shutter 307 is shown placed between the laser light source 305 and the fiber 314.

The laser output from fiber 314 is passed through a bandpass filter 318 to remove any fiber-induced scattering or luminescence and the filter output is focused by a second laser focus lens 320. Once focused or collimated, the laser beam is reflected by a dichroic beamsplitter plate 322 into the back of an objective lens 260 along the optical axis 331.

In another embodiment, the output of the laser light source 305 is passed through a laser focus lens 310 and is sent directly to the dichroic beamsplitter 322. The laser beam is reflected by the dichroic beamsplitter plate 322 into the back of the objective lens 160 along the optical axis.

The diameter of the laser spot on the sample may be varied to ensure adequate signal to noise ratio ("SNR") for bioagent detection. The spot diameter determines the region of the sample being tested, where a larger spot size results in a larger amount of sample undergoing analysis. The spot diameter also determines the maximum laser power density that can be obtained with a given power laser. Large diameters reduce the power density of the laser hitting the sample.

In one embodiment, the laser light source 305 includes a Nd.YAG pulsed laser light source illuminating the sample at a first wavelength of 1064 nm to produce plasma emitted photons, and illuminates the sample at a second wavelength of 532 nm to produce Raman scattered photons.

The apparatus of the present disclosure includes optical systems for delivering and collecting light. In one embodiment, the laser illumination is delivered to the unknown 325 and scattered photons from the unknown 325 are collected along the same optical axis 331. In another embodiment, the laser illumination is delivered to the unknown 325 and plasma emitted photons from the unknown 325 are collected along the same optical axis 331. In yet another embodiment, the laser illumination is delivered to the unknown 325 and scatter photons and plasma emitted photons from the unknown 325 are collected along the same optical axis. A first optical system delivers light and includes the laser line filter 318, the laser focus lens 320, the beam splitter 322 and the objective lens 260. A second optical system also includes the beam splitter 322 and the objective lens 260 as well as the laser reject filter 328 and signal focus lens 330. The collected light is delivered to spectrometer 340 through a fiber array spectral translator 334.

Figure 4:
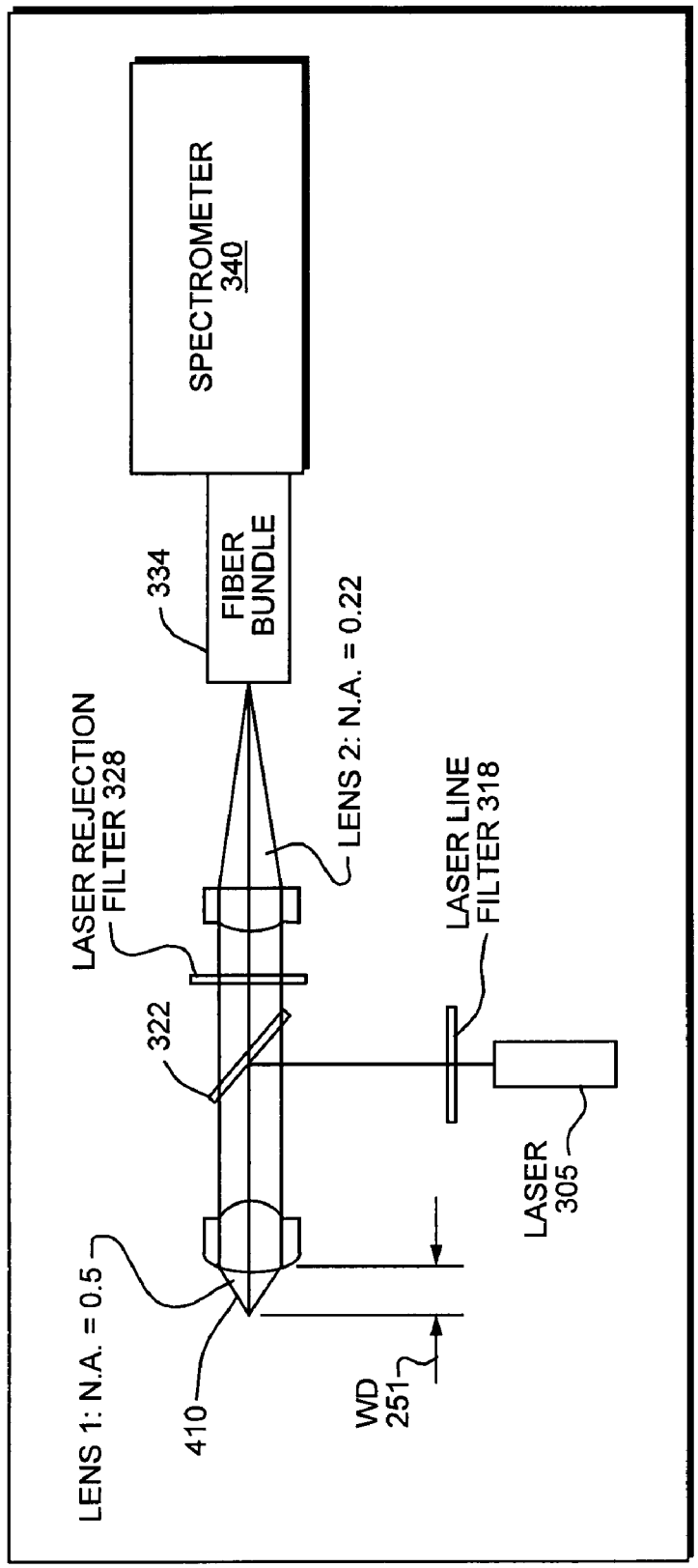
FIG. 4 illustrates an embodiment of the present disclosure

The objective lens 260 is configured to collect as much of the scattered light, reflected light, emitted light or plasma emitted light produced by the sample (not shown) as far as possible from the sample (not shown) as illustrated in FIG. 4. The collection efficiency of lens 260 is expressed in a quantity called the numerical aperture (NA) 410 of the lens. A higher NA means that the objective lens 260 collects light from a larger solid angle from the sample (not shown). The objective lens 260 will also operate at a large working distance (WD) 251—i.e., the distance between the lens and the sample. As the numerical aperture of the objective lens 260 increases, the working distance 251 decreases. In one embodiment, the objective lens 260 has a numerical aperture of 0.5 and operates at a working distance 251 of 6 millimeters. Typical NA range: 0.1 to 0.95. Large working distance reduces likelihood of optics damage during positioning.

Referring again to FIG. 3, the apparatus of the present disclosure includes a fiber array spectral translator device 334 coupled to the sensor unit 130 via fiber position device 332 and a spectrometer 340. The second optical system is used to collect the scattered Raman photons or plasma emitted photons from the objective lens 260, into the fiber array spectral translator 334. The second optical system also includes the beam splitter 322 and the objective lens 260 as well as the laser reject filter 328 and signal focus lens 330. The collected photons are passed from the fiber array spectral translator 334 onto the entrance slit 338 of the spectrometer 340. The dichroic beam splitter 322 serves to reject most of the excitation laser light from entering fiber array spectral translator 334.

Figure 5B:
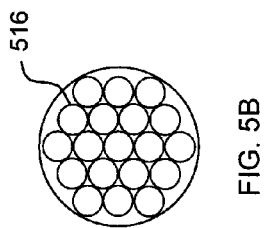
FIGS. 5A and 5B illustrate an exemplary fiber array spectral translator device.
Figure 5A:
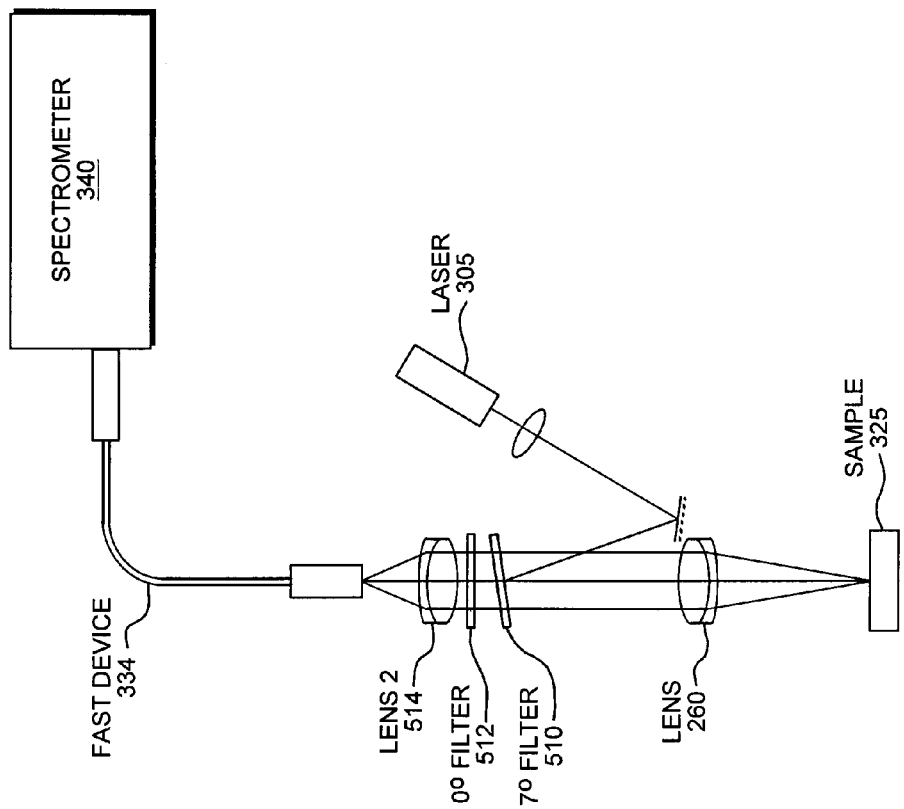

Using the fiber array spectral translator ("FAST") device 334, the apparatus acquires up to thousands of full spectral range, spatially resolved Raman spectra simultaneously. With reference to FIG. 5A, the FAST device 334 is shown relative to laser 305 and objective lens 260. The FAST device 334 is optically coupled to a first filter 510, a second filter 512 a second lens 514. The first lens 260 acts as a collecting lens which focuses the illumination source onto the sample 504 and collects photons. Photons having the same wavelength as the laser will be blocked by filter elements 510 and 512. Lens 260 collimates the photons produced by the sample projecting the photons into infinity. The second lens 514 is used in combination with the first lens 260 to form images at the final focal plane of the second lens 514. The first end of the fiber bundle 516 is comprised of a two dimensional non-linear array of fiber bundles, FIG. 5B. The second end of the fiber bundle 516 is comprised of a curvilinear array of fibers wherein curvilinear may include a straight line as well as a curved line configurations.

Referring to FIG. 3, the collected light is focused onto the first end of the FAST device 334. The one dimensional fiber array 335 is coupled to spectrometer 340 through fiber position device 336. In one embodiment, the fiber array spectral translator 334 may have 19 collection fibers. The entrance slit of the spectrometer 338 is optically coupled to the FAST device 334 to disperse scattered photons and generate a plurality of spatially resolved Raman spectra and a plurality of spatially accurate wavelength resolved images. A two-dimensional array of detection elements or detector 341 is optically coupled to the spectrograph 340 to detect spectral data. The detector 341 could include detectors such as CCDs, CMOS, CIDs (charge injection device), diode arrays, photomultiplier tube (PMT), PMT array, or avalanche photodiode. In one embodiment, the spectrometer 340 operates in an imaging mode generating a plurality of spatially resolved Raman spectra, a plurality of spatially resolved atomic spectra or a plurality of spatially resolved atomic emission spectra. In another embodiment, spectrometer 340 operates in a non-imaging mode, where the response from all of the fibers in the FAST device 334 is added together to generate a composite spectrum for the unknown in the region of interest. In one embodiment, the spectrometer 340 includes a Raman dispersive spectrometer. In another embodiment, the spectrometer includes an atomic emission spectrometer. Processor 342 extracts the spectral/spatial information that is embedded in a single CCD image frame of detector 341.

Referring still to FIG. 3, the apparatus of the present disclosure may include a light shield 326 attached to the sensor unit 130 to reduce the collection of ambient light by the optical system including, for example, the objective lens 260. The light shield 326 should conform to various surface textures including liquids. In one embodiment, the light shield 326 has a bellows-type design. In another embodiment, a light shield has a large cross section. In another embodiment, a secondary light shield may be used to reduce the amount of ambient light from a relatively far distance.

Processor 342 controls the operation of the sensor unit 130 the fine positioning device 200 the force sensor 265, data acquisition, spectral processing and spectral library search functions. The processor 342 may be connected to the sensor unit 130 using Ethernet, serial or other standardized communication protocols.

Processor 342 also executes instructions that apply data analysis algorithms to the plurality of spatially resolved Raman spectra and the plurality of spatially accurate wavelength resolved images generated by the spectrometer 340. The algorithm includes spectral library search algorithms such as those that are well known to those of skill in the art. In one embodiment, the algorithm includes a spectral unmixing algorithm for the analysis of heterogeneous mixtures. A spectral unmixing metric is disclosed in U.S. patent application Ser. No. 10/812,233 entitled "Method for Identifying Components of a Mixture via Spectral Analysis," filed Mar. 29, 2004 which is incorporated herein by reference in its entirety. In this embodiment, the spectral unmixing metric compares the spectral information generated by the sensor unit 130 to reference data in one or more spectral libraries. Sensor unit 130 acquires a set of mixture spectra from the region of interest. The mixture spectra define an n-dimensional data space, where n is the number of points in the spectra or images. In one embodiment, 19 mixture spectra are acquired by sensor unit 130. Principle component analysis (PCA) techniques are applied to the n-dimensional data space to reduce the dimensionality of the data space. The dimensionality reduction step results in the selection of m eigenvectors as coordinate axes in the new data space. The library reference data are compared to the reduced dimensionality data space generated from the sensor unit 130 using target factor testing techniques. Each library reference data is projected as a vector in the reduced m-dimensional data space. An angle between the library vector and the data from sensor unit 130 results from target factor testing. This is performed by calculating the angle between the library reference data and the sensor generated data set. In one embodiment, an Euclidean distance metric is used to determine the distance between the library reference data set and the sensor generated data set. In another embodiment, Mahalanobis distance metric is used to determine the distance between the library reference data set and the sensor generated data set. Those spectral library members that have the smallest angles with the data space are considered as potential members or candidates, of the mixture and are submitted for further testing. The spectral library members are ranked and every combination of the top y members is considered as a potential solution to the composition of the mixture. A multivariate least-squares solution is then calculated for each of the candidate combinations. Finally, a ranking algorithm is applied to each combination and is used to select the combination that is most likely the set of pure components in the unknown.

Figure 6:
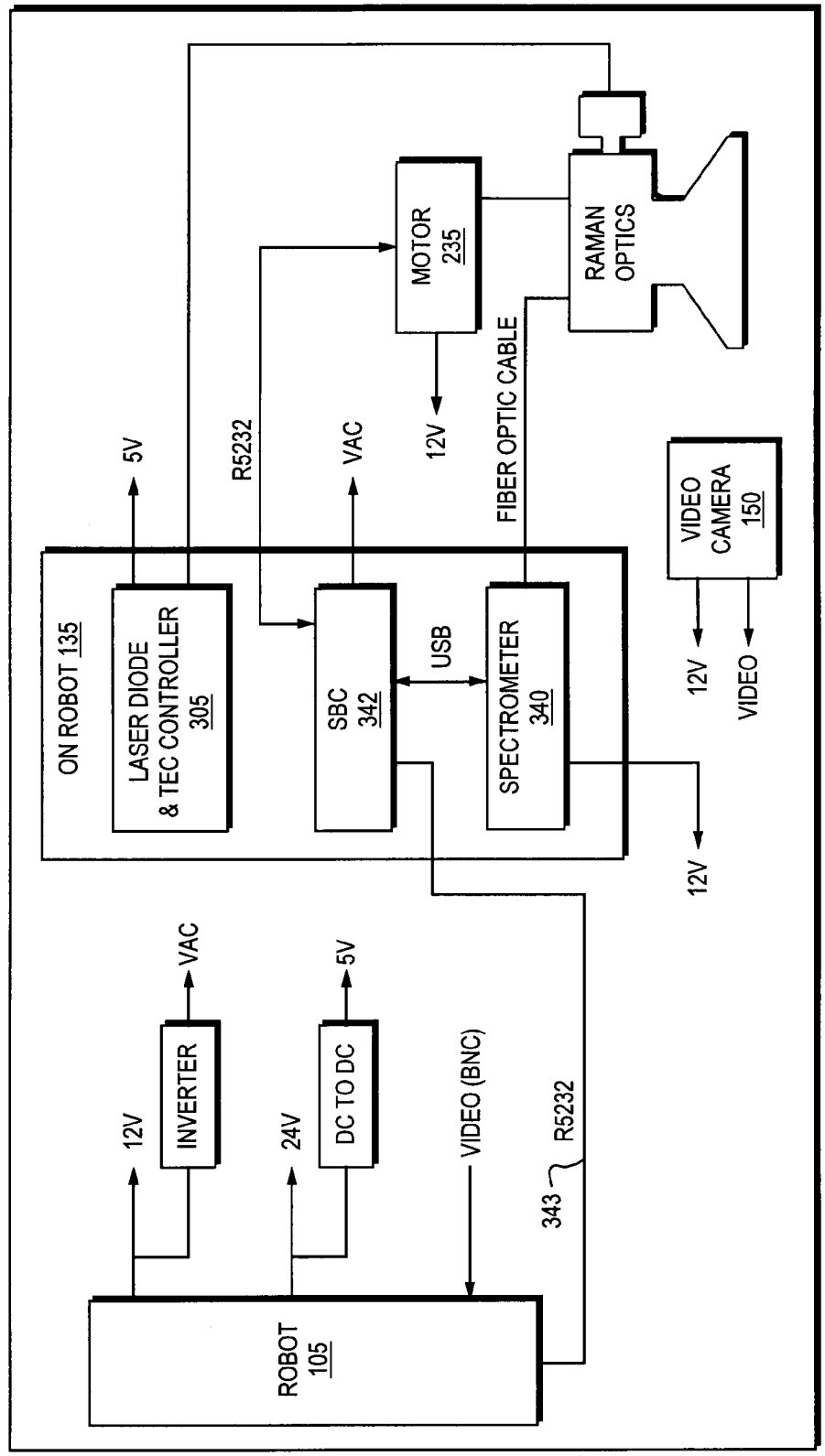
FIG. 6 illustrates an electric schematic of an apparatus of the present disclosure.

FIG. 6 illustrates the electrical schematic of apparatus 100. The robot chassis 105 communicates with processor 342 in instrument package 135 through a RS232 link. The stepper motor and video camera are located on the robotic arm 120. Instrument package 135 includes laser source 305, processor 342 and spectrometer 340.

Figure 7:
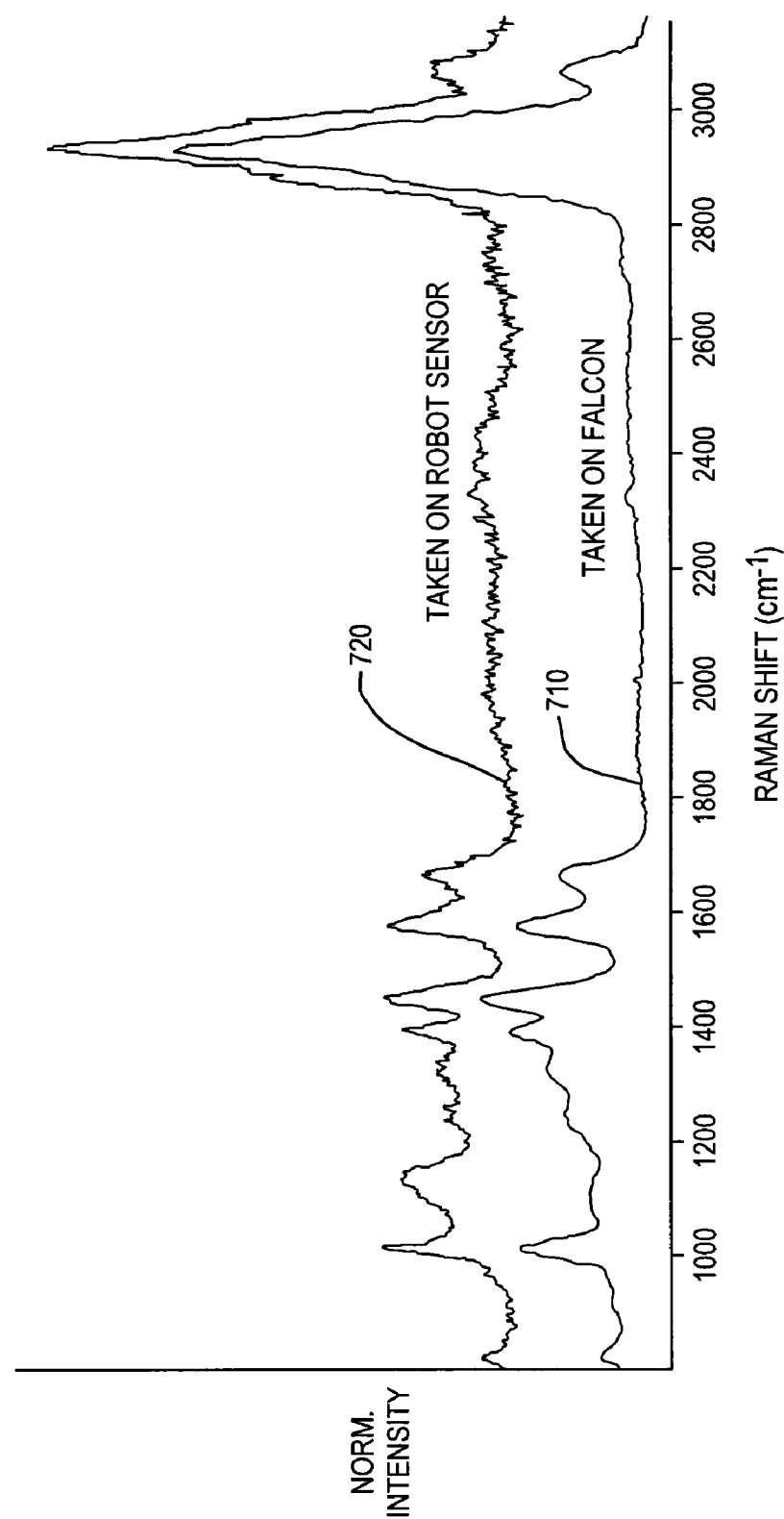
FIG. 7 illustrates Raman spectra of *Bacillus thuringiensis* (Bt) obtained using a device based on the present disclosure.
Figure 8:
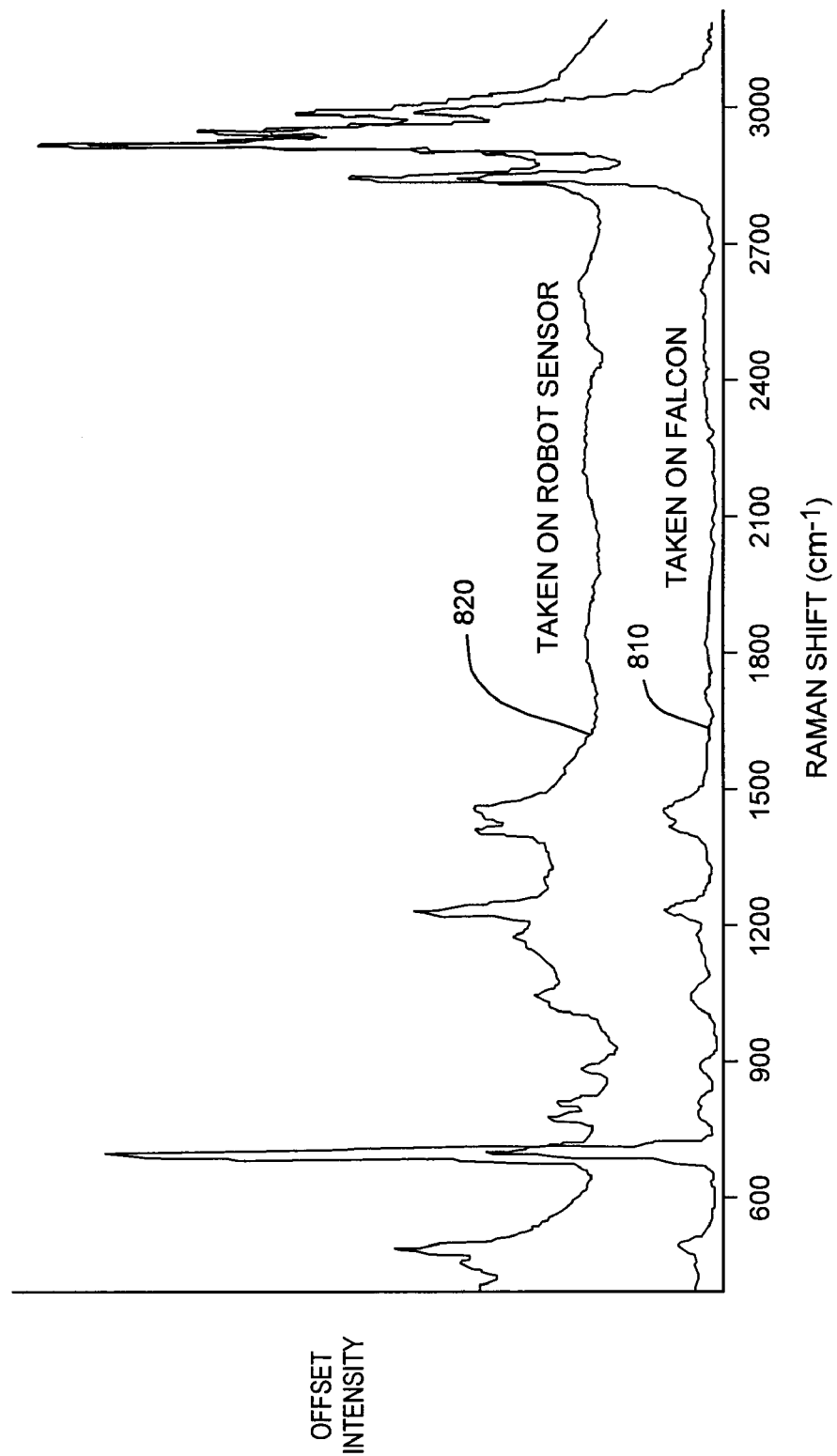
FIG. 8 illustrates Raman spectra of Dimethyl methylphosphonate obtained using a device based on the present disclosure.

FIG. 7 illustrates Raman spectra of *Bacillus thuringiensis* (Bt). Spectrum 710 taken with a FALCON™ microscope system of ChemImage Corp. and Raman spectrum 720 was obtained using a prototype sensor unit of the present disclosure. *Bacillus thuringiensis* (Bt) was chosen to simulate anthrax (*Bacillus anthracis*). Bt is a member of the same family as anthrax and also has the ability to form spores just like anthrax. Testing of the RBI breadboard was done with the spore form of Bt sourced from the Edgewood Chemical and Biological Center. The operating specification for each instrument is shown in Table 1.

TABLE 1

| | FALCON | Robot Sensor |
|---|---|---|
| Agent/Particle Size (μm) | Bt/Single Spores | Bt/Single Spores |
| Est. Concentration (PPFOV) | ~100 | 180 |
| Sample Origin | ECBC | ECBC |
| Laser Wavelength (nm)/ Lens/NA | 532/100x Objective/ 0.95 | 532/Aspheric Lens/ 0.50 |
| Laser Spot Diameter (μm) | 25 | 133 |
| Laser Power Output (mW)/ Power Density (W/cm$^2$) | 20/4.07 × $10^3$ | 12/86.4 |
| Spectral Resolution (cm$^{-1}$) | 20 | 10 |
| Estimated Cross-Sections Raman/Fl (cm2/sr * spore) | 1 * $10^{-16}$/1 * $10^{-14}$ | |
| Time to Photobleach (secs) | 300 | 300 |
| Integration Time (secs)/# Avgs | 17/5 | 10/10 |
| File Name | 060103_RA_04_ BT_SPOT_100X_ RS_RO I9 | 051227_CWG_ BT_1 0S_AVG10_06 |
| SNR (maximum) | 236.6 | 62.3 |

FIG. 8 illustrates Raman spectra of Dimethyl methylphosphonate ("DMMP"). Spectrum 810 taken with a FALCON™ microscope system of Chemimage Corp. and Raman spectrum 820 was obtained using a prototype sensor unit of the present disclosure. DMMP was selected to simulate the detection of G-type nerve agents (i.e. Sarin, Soman). Reagent grade DMMP was purchased from Sigma Aldrich and was analyzed through the wall of a 2 mL sealed glass vial. The operating specification for each instrument is shown in Table 2.

TABLE 2

| | FALCON | Robot Sensor |
|---|---|---|
| Material | DMMP | DMMP |
| Laser Wavelength (nm)/ Lens/NA | 532/20x Objective/ 0.46 | 532/Aspheric Lens/ 0.50 |
| Laser Spot Diameter (mm) | 25 | 133 |

TABLE 2-continued

|  | FALCON | Robot Sensor |
|---|---|---|
| Laser Power Output (mW)/Power Density (W/cm2) | 10/7.88 × 10$^1$ | 12/86.4 |
| Spectral Resolution (cm$^{-1}$) | 20 | 10 |
| Time to Photobleach (secs) | 0 | 0 |
| Integration Time (secs)/# Avgs | 110 | 10/10 |
| File Name | 051123_AJD_05_DMMP_FALCON_NIST_BASE_TRUNC | 051227_CWG_DMMP_NA0-5_3S_AVG10_08 |
| SNR (maximum) | 225 | 129.2 |

Figure 9:
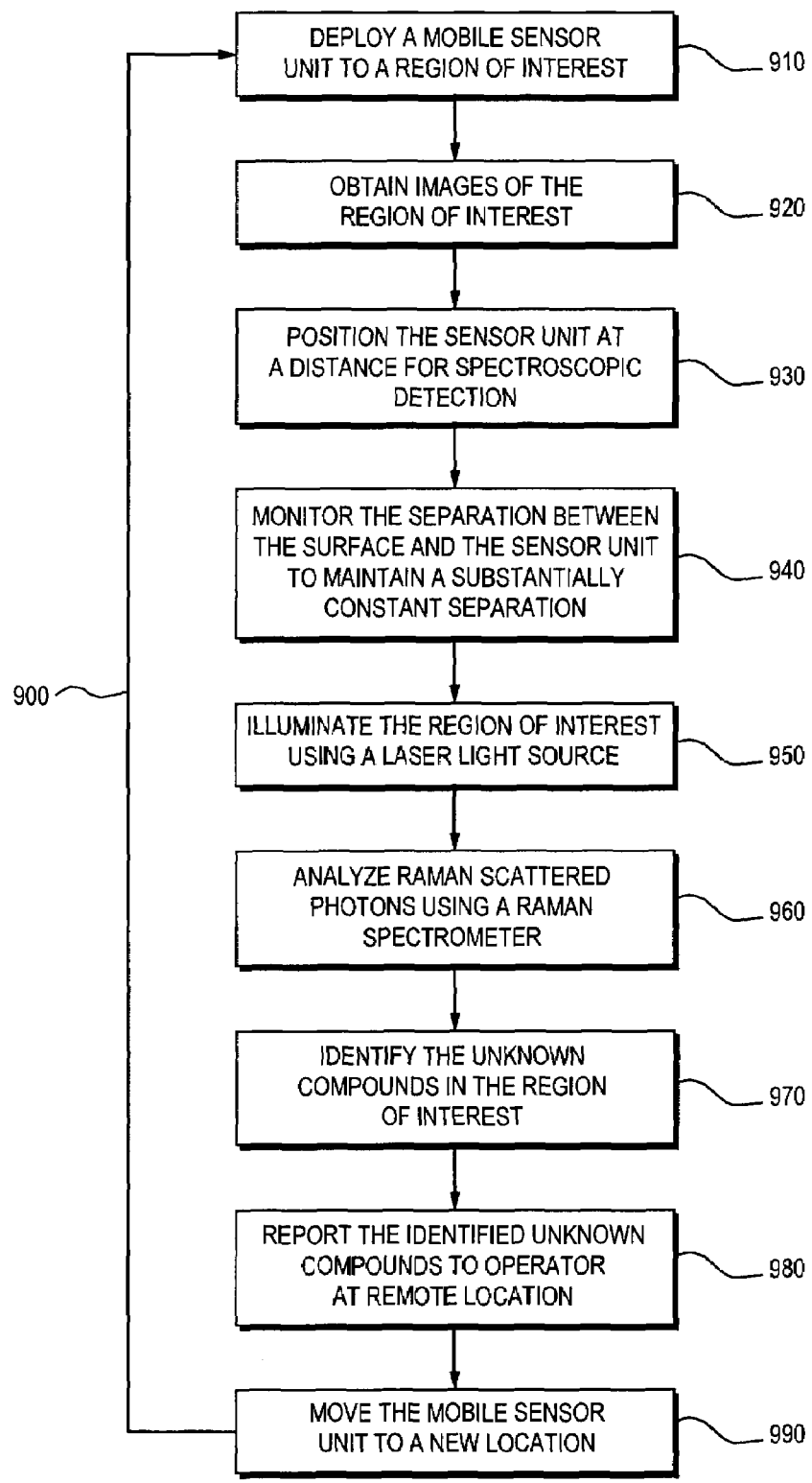
FIG. 9 is a flow chart illustrating a method of the present disclosure.

FIG. 9 illustrates a flow chart of a method of the present disclosure. In step 910, mobile sensor 100 is deployed to survey the region of interest for the presence of hazardous material in the event of suspected chemical or biological contamination. Using an imaging device (not shown), an operator at a remote location (not shown), uses an image capture device located on the mobile sensor of FIG. 1 to obtain images of the region of interest, in step 920. In step 930, the sensor unit 130 is positioned on the surface using a fine positioning device 200 at a distance required for spectroscopic measurement. When the sensor unit 130 is positioned in the region of interest, the separation between the sensor unit 130 and surface 210 is monitored to maintain the separation substantially constant, in step 940. In step 950, the region of interest is illuminated, using a laser light source 305, to produce Raman scattered photons. In step 960, the Raman scattered photons are analyzed using Raman spectroscopy to produce a plurality of spatially resolved Raman spectra or a plurality of spatially accurate wavelength resolved images. In step 970, an algorithm, such as Euclidean distance metric or a spectral unmixing metric, is applied to Raman data to identify the unknown compound(s) in the region of interest. In step 980, the identity of the unknown is reported to an operator at a remote location. The sensor unit is moved to a new location in step 990 and the assay process repeated at step 900.

The present disclosure may be embodied in other specific forms without departing from the spirit of the disclosure. Accordingly, reference should be made to the appended claims, rather than the foregoing specification, as indicating the scope of the disclosure. Although the foregoing description is directed to the preferred embodiments of the disclosure, it is noted that other variations and modification will be apparent to those skilled in the art, and may be made without departing from the spirit or scope of the disclosure.

What is claimed is:

1. An apparatus comprising:
a vertically-movable robotic arm; and
a vertically-movable sensor unit operatively coupled to said robotic arm and having a monitoring mechanism configured to physically contact a surface in a region of interest, wherein said monitoring mechanism includes:
at least one rod configured to be placed in physical contact with said surface through vertical motion of said sensor unit,
a force sensor coupled to said at least one rod to generate an output signal based on contact force between said at least one rod and said surface, and
a feedback mechanism coupled to said force sensor to receive said output signal and to maintain said output signal substantially constant by adjusting vertical separation between said sensor unit and said surface in the region of interest, thereby maintaining said separation substantially constant so as to compensate for vertical movement of said robotic arm during an analysis of said region of interest.

2. The apparatus of claim 1, further comprising:
a fine positioning device positioned between the sensor unit and the robotic arm for incrementally moving the sensor unit relative to said surface in said region of interest.

3. The apparatus of claim 2, wherein said fine positioning device has a tolerance of 40 micrometers from the sensor unit located above the surface.

4. The apparatus of claim 1, further comprising at least one of the following imaging devices to obtain images of said region of interest:
a visible light video capture device;
a fluorescence imaging device;
an NIR (Near Infrared) imaging device;
an MIR (Mid Infrared) imaging device;
a UV (Ultraviolet) imaging device;
a hyperspectral imaging device; and
a tera Hertz (THz) imaging device.

5. The apparatus of claim 1, further comprising a LIBS (Laser Induced Breakdown Spectroscopy) device to target said region of interest for an unknown sample.

6. The apparatus of claim 1, further comprising a laser light source configured to illuminate the surface having an unknown sample, to thereby produce scattered photons from different locations on or within the unknown sample.

7. The apparatus of claim 6, further comprising:
a fiber array spectral translator device coupled to said sensor unit, said device includes a two-dimensional array of optical fibers drawn into a one-dimensional fiber stack so as to effectively convert a two-dimensional field of view into a curvilinear field of view;
wherein said sensor unit includes:
a first optical system coupled to said laser light source to direct light to the unknown sample;
a second optical system that collects said scattered photons, and directs the collected scattered photons to said fiber array spectral translator device;
wherein said fiber array spectral translator device outputs said collected scattered photons received from said second optical system; and
a light shield that reduces ambient light collected by the second optical system.

8. The apparatus of claim 7, further comprising a spectroscopic detector that identifies the unknown sample within the region of interest.

9. The apparatus of claim 8, wherein said spectroscopic detector comprises:
a spectrograph coupled to said one-dimensional fiber stack of said fiber array spectral translator device, wherein an entrance slit of the spectrograph is coupled to said one dimensional fiber stack to disperse said scattered photons output by the fiber array spectral translator device to generate a plurality of spatially resolved Raman spectra; and
a two dimensional array of detection elements, coupled to said spectrograph, that detects the plurality of spatially resolved Raman spectra generated by said spectrograph.

10. A method comprising:
placing a vertically-movable sensor unit adjacent to a surface in a region of interest using a vertically-movable robotic arm;

placing at least one rod in physical contact with said surface through vertical motion of said sensor unit;

detecting contact force between said at least one rod and said surface using a force sensor coupled to said at least one rod so as to generate an output signal;

receiving said output signal using a feedback mechanism coupled to said force sensor; and maintaining said output signal substantially constant by adjusting vertical separation between said sensor unit and said surface in the region of interest using said feedback mechanism, thereby maintaining said separation substantially constant so as to compensate for vertical movement of said robotic arm during an analysis of said region of interest.

11. The method of claim 10, further comprising:

positioning the sensor unit, using a fine positioning device, said fine positioning device having a tolerance of 40 micrometers from the sensor unit located above the surface.

12. The method of claim 10, further comprising:

obtaining images of the region of interest, using an imaging device.

13. The method of claim 10, further comprising:

illuminating the region of interest having an unknown sample using a laser light source, to thereby produce scattered photons from different locations on or within the unknown sample.

14. The method of claim 13, further comprising:

collecting, via an optical system, scattered photons produced by the unknown sample;

outputting said collected photons using a fiber array spectral translator device, wherein said device comprises a two-dimensional array of optical fibers drawn into a one-dimensional fiber stack so as to effectively convert a two-dimensional field of view into a curvilinear field of view;

analyzing the scattered photons, produced by the unknown sample, using Raman spectroscopy to produce a plurality of spatially resolved Raman spectra; and applying an algorithm to the plurality of spatially resolved Raman spectra to thereby identify the unknown sample in the region of interest.

15. The method of claim 14, further comprising:

reducing ambient light collected by said optical system using a light shield.

16. The method of claim 12, wherein said imaging device is at least one of the following:

a visible light video capture device;

a fluorescence imaging device;

an NIR (Near Infrared) imaging device;

an MIR (Mid Infrared) imaging device;

a UV (Ultraviolet) imaging device;

a hyperspectral imaging device; and a tera Hertz (THz) imaging device.

\* \* \* \* \*